United States Patent [19]

Elliott et al.

[11] Patent Number: 5,200,217

[45] Date of Patent: * Apr. 6, 1993

[54] ENZYME INFUSION PROCESS FOR PREPARING WHOLE PEELED CITRUS FRUIT

[75] Inventors: Robert S. Elliott, Wildomar; Julia C. Tinibel, Pomona, both of Calif.

[73] Assignee: Sunkist Growers, Inc., Sherman Oaks, Calif.

[*] Notice: The portion of the term of this patent subsequent to Mar. 19, 2008 has been disclaimed.

[21] Appl. No.: 783,013

[22] Filed: Oct. 25, 1991

[51] Int. Cl.⁵ ............................................. A23L 1/05
[52] U.S. Cl. ...................................... 426/50; 426/52; 426/287; 426/482; 426/616
[58] Field of Search ................... 426/50, 52, 287, 482, 426/616

[56] References Cited

U.S. PATENT DOCUMENTS

| | | |
|---|---|---|
| 1,469,650 | 10/1923 | Sletto . |
| 1,553,630 | 9/1925 | Polk . |
| 1,601,027 | 9/1926 | Lefevre . |
| 1,872,732 | 8/1932 | Goranson et al. . |
| 1,920,095 | 7/1933 | McCall . |
| 2,224,235 | 12/1940 | Rogers . |
| 2,277,003 | 3/1942 | Polk, Jr. . |
| 2,283,290 | 5/1942 | Savage . |
| 2,286,649 | 6/1942 | Rogers . |
| 2,300,312 | 10/1942 | Polk, Sr. . |
| 2,465,223 | 3/1949 | Gross . |
| 2,551,156 | 5/1951 | Polk, Sr. et al. . |
| 2,570,071 | 10/1951 | Polk, Sr. et al. . |
| 2,639,746 | 5/1953 | Gross . |
| 2,699,191 | 1/1955 | De Back et al. . |
| 2,776,690 | 1/1957 | Warren . |
| 3,237,299 | 3/1966 | Gibbs . |
| 3,347,678 | 10/1967 | Villadsen . |
| 3,473,588 | 10/1969 | Loveland . |
| 3,515,188 | 6/1970 | Morikawa et al. . |
| 3,618,651 | 11/1971 | Hart et al. . |
| 3,700,017 | 10/1972 | Vincent et al. . |

(List continued on next page.)

OTHER PUBLICATIONS

Kosuke Aizawa, Takashisa Tozuka, Takenori Onishi and Hajime Koga, "Segment-skin Removal of Mandarin Oranges with Enzyme":, *Shokuhin Kaihatsu*, (1975).

Bruemmer, Joseph H. and Griffin, Alicia W., "Sectioning Grapefruit by Enzyme Digestion," *Proc. Fla. State Hort. Soc.* 91, 1978, pp. 112-114.

Citrograph—"Vacuum Cleaned" Fresh Citrus—Jun. 1989, pp. 203-204, vol. 74, No. 8.

*Primary Examiner*—Joseph Golian
*Assistant Examiner*—Leslie Wong
*Attorney, Agent, or Firm*—Stephen J. Koundakjian; Paul Del Giudice

[57] ABSTRACT

A process for peeling fresh citrus fruit to provide peeled whole fruit, with ease of peeling and with limited amounts of adhering albedo. The fresh citrus fruit are initially chilled to a temperature well below room temperature, preferably less than about 10 degrees C. The chilled fruit are then scored so as to penetrate the albedo layer, but not the underlying juice sections, and the scored fruit are then immersed in an aqueous solution of a pectinase enzyme at an initial temperature of about 35 degrees C. The enzyme solution is then infused into the fruit, and after holding the infusion-treated fruit in the solution for a prescribed time period, without application of additional heat, the peel can be readily removed from the whole fruit. Chilling the fruit before infusing the pectinase enzyme allows the core of the fruit to reach a temperature low enough to insure that the pectinase enzyme retains its full effectiveness only in the region of the peel and not at the membrane connecting together the segments of the fruit. This insures that the segments remain connected together, to provide peeled whole fruit.

14 Claims, No Drawings

| | | | |
|---|---|---|---|
| 3,853,050 | 12/1974 | Schier | 99/590 |
| 3,970,762 | 7/1975 | Askienazy et al. | 426/287 |
| 3,982,037 | 9/1976 | Weaver et al. | 426/482 |
| 3,982,482 | 9/1976 | Webb et al. | 99/491 |
| 4,065,582 | 12/1977 | Webb et al. | 426/231 |
| 4,109,021 | 8/1978 | Loveland | 426/482 |
| 4,130,668 | 12/1978 | Otsuka et al. | 426/287 |
| 4,161,459 | 7/1979 | Otsuka et al. | 252/352 |
| 4,220,670 | 9/1980 | Mohri et al. | 426/287 |
| 4,275,648 | 6/1981 | Mouri et al. | 99/483 |
| 4,279,263 | 7/1981 | Pulliam | 134/111 |
| 4,284,651 | 8/1981 | Bruemmer | 426/50 |
| 4,318,339 | 3/1982 | Sage | 99/589 |
| 4,490,335 | 12/1984 | Marey et al. | 422/269 |
| 4,569,850 | 2/1986 | Harris et al. | 426/482 |
| 4,720,388 | 1/1988 | Pierce et al. | 426/231 |
| 4,729,299 | 3/1988 | Hatch | 99/491 |
| 4,771,682 | 9/1988 | Ishikawa | 99/593 |
| 4,839,181 | 6/1989 | MacMurray et al. | 426/237 |
| 5,000,967 | 3/1991 | Adams et al. | 426/50 |

ENZYME INFUSION PROCESS FOR PREPARING WHOLE PEELED CITRUS FRUIT

BACKGROUND OF THE INVENTION

1. Field of the Invention

This invention relates generally to processes for peeling fresh citrus fruit and, more particularly, to such processes that utilize the infusion of a pectinase enzyme into the peel of the fruit.

2. Description of the Related Art

An example of a pectinase enzyme-infusion process of this particular kind is described in U.S. Pat. No. 4,284,651 to Bruemmer. In the described process, washed citrus fruit such as oranges and grapefruit are initially heated to a surface temperature of about 40 to 60 degrees C. and a core temperature of about 20 to 40 degrees C., after which the peel surface of the fruit is scored so as to penetrate the fruit's albedo or white layer, but not penetrate the fruit's juice segments. An aqueous solution of a pectinase enzyme is then vacuum infused into the fruit's albedo, at a vacuum of about 25 to 30 inches of mercury. After incubating the fruit for a period of 15 minutes to 2 hours, at a temperature of about 30 to 60 degrees C., maintained by application of external heat, the peel and other membrane material are removed from the fruit and the exposed fruit segments are separated from each other, with most of the segment membranes remaining intact. The fruit segments can then be refrigerated for extended durations, while substantially retaining a fresh fruit flavor and appearance.

The process described briefly above has proven to be generally satisfactory in providing individual fruit segments having a substantially fresh fruit flavor and appearance. There is a need, however, for a process whereby fruit remains whole during the peeling process rather than tending to become segmented. Maintenance of the fruit in a whole state during the peeling process facilitates more rapid removal of the peel and permits mechanization of the process. In addition, such peeled whole fruit can be attractively packaged and sold for applications, such as "cartwheel" (i.e., transverse) slicing, to which segmented fruit does not readily lend itself. Peeled whole fruit also eliminates the problem of the loss of separated segments that are damaged and/or carry adhered albedo. The process described briefly above—which clearly appears to have been designed specifically to produce fruit segments—has not been satisfactory in reliably providing such peeled whole fruit.

It should, therefore, be appreciated that there is a need for an improved process for enzyme peeling fresh citrus fruit, which is effective in providing peeled whole fruit, with ease in peeling and little adhering albedo. The present invention fulfills this need.

SUMMARY OF THE INVENTION

The present invention resides in a process for peeling fresh citrus fruit, in which a pectinase enzyme solution is infused into the fruit peel in a way that enables the peel to be removed with little adhered albedo while maintaining the membrane that keeps the fruit whole. The process of the invention achieves these improved results by chilling the fruit before infusing the pectinase enzyme and maintaining the core of the fruit at a relatively low temperature during remainder of the peel removal process. Because the only application of heat is to warm the enzyme solution prior to infusion, this process also significantly reduces production costs and conserves energy.

More particularly, the process of the invention includes an initial step of maintaining the core and surface temperatures of the fresh citrus fruit at a temperature of less than about 20 degrees C. The peel surface of the fruit is then broken, e.g., scored, so as to penetrate the fruit's albedo layer, but not its juice segments An aqueous solution of pectinase enzyme at a temperature of about 35 degrees C. is then vacuum- or pressure-infused into the scored fruit, after which the fruit is held in the aqueous solution without application of additional heat for a prescribed duration, to allow the pectinase to break down the pectin present in the albedo. During the holding period, the pectinase enzyme solution cools while the temperature of the core slowly rises to a temperature no greater than about 25 degrees C., so that any pectinase that reaches the core will have lost much of its effectiveness, and the membranes that connect together the segments of the fruit will remain largely intact. The fruit peel can then be readily removed without disturbing the segment membranes, to yield the peeled whole fruit. Operating at these lower temperatures also reduces the degree of refrigeration required later to lower the fruit's temperature to that required for subsequent storage and shipping, typically about 2 degrees C.

Other features and advantages of the present invention will become apparent from the following description of the preferred process, which illustrates, by way of example, the principles of the invention.

DESCRIPTION OF THE PREFERRED PROCESS

The invention resides in a process for preparing whole peeled citrus fruit from fresh unpeeled citrus fruit using an aqueous solution of a pectinase enzyme. The solution is infused into the albedo, or white layer, of the citrus fruit peel, to break down the pectin contained in the albedo and thereby to facilitate an easy removal of the peel. Pectinase becomes effective at elevated temperatures, beginning generally in range of about 20 to 25 degrees C., with peak efficiency at about 45 to 50 degrees C. Pectinase is a natural product of mold growth and is approved for food use by the United States Food and Drug Administration. Pectinase is commonly used commercially in a variety of food applications, such as clarification and stabilization of fruit juices. The process of the invention can be used particularly effectively with Valencia and navel oranges, grapefruit and lemons.

In an initial step of the process, the core and surface of a batch of fresh citrus fruit are chilled to a temperature of less than about 10 degrees C. The peel of the fresh citrus fruit is then scored or otherwise broken so as to barely penetrate the peel's thick albedo layer, but not to penetrate any of the underlying fruit segments or segment membranes. For example, the fruit can each be scored into six substantially equal-sized wedge sections, extending from the stem to the blossom end. Many other ways of breaking the peel also are suitable, including scoring the peel with a single- or multiple-ring pattern or a spiral pattern, and even grating or randomly scratching the peel. In particular, where the fruit is scored by means of an equatorial slit, peel removal can more easily be accomplished mechanically, and the resulting hemispherical peel shells can readily be packaged and processed for secondary product utilization.

The scored fruit are then placed in an aqueous solution of pectinase enzyme, preparatory to the infusion. NOVO Pectinex 5XL is one suitable pectinase enzyme, and it can be used at a concentration of 1000 ppm, i.e., 1.0 milliliter per liter, in tap water. Another suitable pectinase is NOVO Pectinex Ultra SP, and it can also be used at a concentration of 1000 ppm, i.e., 1.0 milliliter per liter, in tap water. It will be noted that throughout this discussion, enzyme manufacturer names are shown fully capitalized, as in "NOVO". This is for the convenience of practitioners seeking to obtain pectinase enzymes necessary to practice the teachings herein given.

The concentration of the pectinase enzyme used may vary somewhat. In practice, it has been observed that consistently successful peeling of early season, fresh citrus fruit requires higher enzyme concentration, due to the fact that citrus peels tend to loosen naturally as the harvest season progresses. Thus, the concentrations given above are average seasonal values. Early in the season the concentration must often be doubled, while toward the end of the season it may often be halved.

The pectinase enzyme solution, at an initial temperature of about 35 degrees C., is infused into the scored fruit using either a vacuum process or a pressure process. In the case of a vacuum infusion, the fruit and enzyme solution are placed together in a vacuum chamber and a vacuum of 25 to 30 inches of mercury is then applied, to draw off air from the fruit peel. Releasing the vacuum then infuses the enzyme solution into the minute spaces in the peel previously occupied by air. A medium-sized orange (size 113) typically will draw in about 30 milliliters of the enzyme solution.

In the case of pressure infusion, on the other hand, the fruit and enzyme solution are placed together in a pressure chamber, and a series of positive pressure pulses, e.g., six to ten, is applied to the chamber. The pressure pulses preferably each have a pressure of about 20 to 40 p.s.i., relative, and a duration of about 15 seconds. The pressure pulses are separated from each other by periods of 0 p.s.i., relative, having durations of about 5 seconds each. Pulsing the pressure is believed to cause the fruit peel to flex, which helps to work the enzyme solution throughout the peel.

The pectinase enzyme-infused fruit are then removed from the vacuum or pressure chamber and held in unheated storage tubs, still immersed in the enzyme solution, for about 20 minutes to about 90 minutes. As in the case of concentration of enzyme in the aqueous solution, the duration of this holding period tends to decrease during the harvest season. Early in the season, the range may be from about 30 minutes to about 90 minutes (depending on the nature and condition of the particular fruit), while at the end of the season, the range may be from only about 20 minutes to about 60 minutes.

This holding period allows the enzyme solution to cool, and the peel and albedo to warm to approximate equilibrium with the peel and albedo, at a relatively steady state temperature where the pectinase enzyme begins to be effective in the peel/albedo region. However the duration of holding is insufficient for the core to warm to a temperature where the pectinase is as effective. This allows the enzyme to break down the pectin in the fruit's albedo, but does not allow the enzyme to break down the pectin in the membrane connecting together the segments of the fruit. The fruit peel can thereafter be readily removed with only minimal amounts of albedo clinging to the whole fruit and without the separation of the segments of the fruit. Because of the lack of damage to the core membranes, the whole peeled fruit maintains its structural integrity, and may therefore be peeled rapidly and, preferably, mechanically without substantial loss of product from tearing and separation.

In accordance with the invention, greatly enhanced production of whole peeled citrus can be realized if the entire process is performed at temperatures substantially lower than those previously used to produce citrus segments. In particular, it has been found that chilling the fruit to well below room temperature (i.e., well below 20 degrees C.) prior to enzyme infusion results in an improved ease in peeling and in a reduced amount of adhering albedo. Processing the fruit at these lower temperatures also eliminates the need for special heating apparatus of the fruit and reduces the degree of refrigeration required later to lower the fruit's temperature to that ordinarily called for in storage and shipping, i.e., typically about 2 degrees C. This significantly reduces the complexity and cost of the process, reduces energy consumption and increases safety.

Although the range of temperatures and duration of storage in the enzyme solution vary somewhat according to the nature and condition of the fruit, as discussed above, the preferred temperatures are a pre-infusion chill temperature to about 5 to 8 degrees C. and an enzyme application temperature of about 35 degrees C., with the fruit cores allowed to slowly rise to a final temperature of only about 24 degrees C.

Since fruit conditions and enzyme activity vary, even these preferred parameters are only approximate, hence the common use of the term "about". Some experimentation, well within the skill of the ordinary practitioner, may be necessary to fix the exact parameters for any particular batch of fruit, within the teachings herein set forth.

The improvements in peeling without the segmenting of the fruit are shown by Examples 1-6, set forth below. In these examples, the size number refers to the number of fruits contained in a California Standard container of approximately 16⅜ by 10-11/16 by 10¼ inch inside dimensions.

EXAMPLES 1-3

Examples 1 to 3 correspond generally with the process described in U.S. Pat. No. 4,284,651 to Bruemmer. In example 1, twelve size-48 navel oranges were preheated in a water bath at 128 degrees F. (53.3 degrees C.) until their interior core temperatures reached a range of 68 to 80 degrees F. (20 to 36.7 degrees C.). The oranges were then removed from the water bath and scored into sections, deep enough to reach the albedo but not damage the orange flesh. The preheated, scored oranges were then infused with 1000 ppm NOVO Pectinex Ultra SPL solution, at 68 degrees F. (20 degrees C.), and the oranges were then incubated in an oven at 91.4 degrees F. (33 degrees C.) for one hour. After peeling, five of the twelve oranges began to segment.

In example 2, twelve size-48 navel oranges were preheated in a water bath at 122 degrees F. (50 degrees C.) until their interior core temperatures reached a range of 77 to 78 degrees F. (25 to 25.6 degrees C.). The oranges were removed from the water bath and scored into sections, deep enough to reach the albedo but not damage the orange flesh. The preheated, scored oranges were then infused with 1000 ppm NOVO Pectinex Ultra SPL solution at 70 degrees F. (21.1 degrees C.).

After infusion, the oranges were removed from the solution and incubated in an oven at 89.6 degrees F. (32 degrees C.) for one hour. After peeling, six of the twelve oranges began to segment.

In example 3, twelve size-48 navel oranges were preheated in a water bath at 115 degrees F. (46.1 degrees C.) until their interior core temperatures reached 69.8 degrees F. (21 degrees C.). The oranges were then removed from the water bath and scored into sections, deep enough to reach the albedo but not damage the orange flesh. The preheated, scored oranges were then infused with 1000 ppm NOVO Pectinex Ultra SPL solution at 74 degrees F. (23.3 degrees C.). The oranges were then incubated in an oven at 95 degrees F. (35 degrees C.) for one hour. After peeling, five of the twelve oranges began to segment.

EXAMPLES 4-6

Examples 4 to 6 correspond to the method of the present invention. In example 4, twelve size-48 navel oranges were held in a cooler at 40 degrees F. (4.4 degrees C.). When removed from the cooler, the oranges had a core temperature of approximately 55 degrees F. (12.8 degrees C.). The peels of the oranges were then perforated and the oranges infused with 1000 ppm NOVO Pectinex Ultra SPL solution at a temperature of 95 degrees of (35 degrees C.). The oranges were left standing in this solution for one hour, unheated, and at the end of the hour had an average interior core temperature of 75 degrees F. (23.9 degrees C.). After peeling, all twelve of the navel oranges remained whole.

In example 5, twelve size-48 navel oranges were removed from a cooler at 40 degrees F. (4.4 degrees C.), at which time they had a core temperature of approximately 49.6 degrees F. (9.4 degrees C.). The peels of the oranges were then perforated and the oranges infused with 1000 ppm NOVO Pectinex Ultra SPL solution at a temperature of 96 degrees F. (35.6 degrees C.). The oranges were left standing in the solution for one hour, unheated, after which time the average inner core temperature was 72.9 degrees F. (22.7 degrees C.). After peeling, eleven of the oranges remained whole, and one navel orange broke into sections, possibly due to the fact that it was found to have been severely freeze damaged and thus dry.

In example 6, twelve size-48 navel oranges were removed from a cooler at 40 degrees F. (4.4 degrees C.), at which time they had an average core temperature of 46.3 degrees F. (7.8 degrees C.). The peels of the oranges were then perforated and the oranges infused with 1000 ppm NOVO Pectinex Ultra SPL solution at a temperature of 96 degrees F. (35.6 degrees C.). The oranges were left standing in this solution for one hour, unheated, after which time the average inner core temperature was 72.8 degrees F. (22.6 degrees C.). After peeling, all twelve of the navel oranges remained whole.

Table 1 summarizes these results showing the number of navel oranges from each example that segmented after being peeled.

TABLE 1

| Example No. | Navel Oranges Out of 12 That Segmented When Peeled |
|---|---|
| 1 | 5 |
| 2 | 6 |
| 3 | 5 |
| 4 | 0 |
| 5 | 1 |
| 6 | 0 |

Examples 1-3: Bruemmer method, U.S. Pat. No. 4,284,651.
Examples 4-6: Method of the present invention.

It will be appreciated that the method of the present invention provides peeled whole fruit that remain intact and do not break apart readily into their constituent sections. A significantly higher proportion of fruit processed according to the invention remain intact, as compared with fruit processed according to known prior techniques. This difference in segmentability seems to be directly related to the inner core temperature of the fruit. Prechilling the fruit, as in the present invention, insures that infused pectinase that reaches the fruit core will have reduced effectiveness and thus be unable to attack the segment membranes sufficiently to cause the fruit to break apart into segments on its own.

Extensive experimentation was also carried out to test various readily available pectinase enzymes in terms of their ability to promote easy and clean peeling of grapefruit, and to compare the texture of the resulting peeled fruit.

Three separate criteria were applied: Peelability, Albedo Remaining and Texture. A score of 1 (best) to 5 (worst) was applied to each individual criterion, which were added to generate an Over-All Score for the particular enzyme tested. The results are summarized in Table 2.

TABLE 2

| Enzyme | Peelability | Albedo Remaining | Texture | Over-All Score |
|---|---|---|---|---|
| GENENCOR 219 | 4 | 4 | 2 | 10 |
| GENECOR HS | 2 | 3 | 5 | 10 |
| GENENCOR 1902 | 1 | 2 | 2 | 5 |
| ROHM D5L | 1 | 2 | 4 | 7 |
| NOVO Spark-L | 4 | 4 | 4 | 12 |
| ROHM Rohapect TF | 3 | 3 | 4 | 11 |
| ROHM Rohapect MAC | 4 | 4 | 5 | 13 |

It should be noted that while GENENCOR 1902 showed the best overall results, this product is still in the experimental stage and consequently not yet in full production. Therefore, ROHM D5L is presently the most acceptable of the readily available pectinase enzymes for use in the fruit peeling process of the present invention.

Although the invention has been described in detail with reference to its presently preferred process, it will be understood by one of ordinary skill in the art that various modifications can be made without departing from the invention. Accordingly, the invention is defined only by the following claims.

We claim

1. A process for preparing whole peeled citrus fruit, comprising the steps of:

maintaining the core and surface temperatures of fresh citrus fruit at a temperature of less than about 20 degrees C.;

breaking the peel surface of the fruit so as to penetrate the albedo layer, but not penetrate the juice sections;

infusing an aqueous solution of pectinase into the fruit;

holding the infusion-treated fruit for a time period which is sufficient to allow the pectinase to break down the pectin present in the albedo layer but is insufficient to raise the temperature of the core of the fruit to above about 25 degrees C.; and removing the peel from the fruit.

2. A process as defined in claim 1, wherein the infusion-treated fruit are held in the step of holding for about 20 minutes to about 90 minutes prior to the following step of removing.

3. A process as defined in claim 1, wherein the step of holding includes a step of storing the infusion-treated fruit in the aqueous enzyme solution for the time period.

4. A process as defined in claim 3, wherein the aqueous solution used in the steps of infusing and holding has an initial temperature of about 35 degrees C.

5. A process as defined in claim 1, wherein in the step of maintaining, the time period is insufficient to raise the core temperature of the fresh citrus fruit to a temperature of more than about 10 degrees C.

6. A process as defined in claim 1, wherein the step of infusing a step of placing the scored fruit with the aqueous solution of pectinase in a vacuum chamber, at a vacuum of about 25 to 30 inches of mercury.

7. A process as defined in claim 1, wherein the citrus fruit are oranges.

8. A process as defined in claim 1, wherein the citrus fruit are grapefruit.

9. A process as defined in claim 1, wherein the citrus fruit are lemons.

10. A process for preparing whole peeled citrus fruit, comprising the steps of:

maintaining the core and surface temperatures of fresh citrus fruit at a temperature of less than about 20 degrees C.;

breaking the peel surface of the fruit so as to penetrate the albedo layer, but not penetrate the juice sections;

immersing the scored fruit in an aqueous solution of pectinase within a vacuum chamber, at an initial temperature of about 35 degrees C., and applying a vacuum to the immersed fruit for a duration sufficient to infuse the pectinase into the fruit;

holding the infusion-treated fruit in the aqueous solution for about 20 minutes to about 90 minutes, to allow the pectinase to break down the pectin present in the albedo, wherein the temperature of the core of the held fruit remains continuously at a temperature of less than about 25 degrees C.; and removing the peel from the fruit.

11. A process as defined in claim 10, wherein the citrus fruit are oranges.

12. A process as defined in claim 10, wherein the citrus fruit are grapefruit.

13. A process as defined in claim 10, wherein the citrus fruit are lemons.

14. A process as defined in claim 10, wherein in the step of maintaining, the core and surface are maintained at a temperature of less than about 10 degrees C.

* * * * *